United States Patent
Klein et al.

(10) Patent No.: US 9,951,031 B2
(45) Date of Patent: Apr. 24, 2018

(54) CONCENTRATED STORAGE-STABLE AQUEOUS OPTICAL BRIGHTENING SOLUTIONS

(75) Inventors: Cedric Klein, Brumath (FR); Frederic Reveaud, Mulhouse (FR); David Puddiphatt, Bradford (GB); Andrew Clive Jackson, Muenchenstein BL (CH)

(73) Assignee: ARCHROMA IP GMBH, Reinach (CH)

( * ) Notice: Subject to any disclaimer, the term of this patent is extended or adjusted under 35 U.S.C. 154(b) by 936 days.

(21) Appl. No.: 13/513,369

(22) PCT Filed: Dec. 1, 2010

(86) PCT No.: PCT/EP2010/007287
§ 371 (c)(1),
(2), (4) Date: Jun. 1, 2012

(87) PCT Pub. No.: WO2011/066955
PCT Pub. Date: Jun. 9, 2011

(65) Prior Publication Data
US 2012/0238171 A1    Sep. 20, 2012

(30) Foreign Application Priority Data

Dec. 2, 2009  (EP) .................................... 09014923
Apr. 23, 2010  (EP) .................................... 10004335

(51) Int. Cl.
*C07D 251/54*   (2006.01)
*D21H 21/30*   (2006.01)

(52) U.S. Cl.
CPC .......... *C07D 251/54* (2013.01); *D21H 21/30* (2013.01); *Y10T 428/249921* (2015.04); *Y10T 442/2582* (2015.04); *Y10T 442/60* (2015.04)

(58) Field of Classification Search
CPC .................... C07D 251/54; D06M 13/358; D06M 13/325; D06M 2101/06; C08K 5/0041;
(Continued)

(56) References Cited

U.S. PATENT DOCUMENTS 3,479,349 A   11/1969   Allison et al.
3,589,921 A   6/1971   Allison et al.
(Continued)

FOREIGN PATENT DOCUMENTS

CH   532686   *   1/1973   ............. A61B 17/80
CH   532686 A      1/1973
(Continued)

OTHER PUBLICATIONS

International Search Report for PCT/EP2010/007287 dated Jan. 18, 2011.
(Continued)

*Primary Examiner* — Jennifer A Steele
(74) *Attorney, Agent, or Firm* — McBee Moore Woodward & Vanik IP, LLC

(57) ABSTRACT

Concentrated storage stable aqueous solutions (S) comprising components (a), (b) and (c), wherein component (a) is at least one optical brightening agent of formula (1), in which the anionic charge on the brightener is balanced by a cationic charge composed of one or more cations selected from the group consisting of hydrogen, alkali metal cation, alkaline earth metal cation, ammonium, ammonium which is mono-, di- or trisubstituted by a $C_{1-4}$ linear or branched alkyl radical and ammonium which is mono-, di- or trisubstituted by a $C_{1-4}$ linear or branched hydroxyalkyl radical, and the concentration of component (a) is 0.08 to 0.3 mol per kg, based on the total weight of the concentrated storage-stable aqueous solutions (S), component (b) is at least one inorganic salt (SA), in a concentration of 2 to 15% by weight, based on the
(Continued)

total weight of the concentrated storage-stable aqueous solutions (S), and component (c) is water, in a concentration of 10% to 88% by weight, based on the total weight of the concentrated storage-stable aqueous solutions (S).

26 Claims, 1 Drawing Sheet

(58) Field of Classification Search
CPC ... C08K 5/005; C08K 5/34092; D06L 3/1207; D06L 4/65; D06L 4/621; D06L 4/664; D06L 4/636; D06L 4/686; D06L 4/693; Y10T 442/2582; C09B 43/16; C09B 23/148; C09B 62/04
USPC ............... 252/301.21, 301.22, 301.29, 8.91; 162/162; 8/648; 442/131–133
See application file for complete search history.

(56) References Cited

U.S. PATENT DOCUMENTS

| | | | | |
|---|---|---|---|---|
| 8,821,688 B2* | 9/2014 | Jackson | ................ | D21H 17/63 106/286.6 |
| 8,845,861 B2* | 9/2014 | Jackson | ................ | D21H 17/63 106/206.1 |
| 2004/0111812 A1 | 6/2004 | Yamaguchi et al. | | |
| 2007/0245503 A1* | 10/2007 | Jackson et al. | ................... | 8/442 |
| 2011/0281042 A1* | 11/2011 | Wild | ............................ | 428/32.1 |

FOREIGN PATENT DOCUMENTS

| | | |
|---|---|---|
| CN | 1498250 A | 5/2004 |
| CN | 101094842 A | 12/2007 |
| EP | 1 378 545 | 1/2004 |
| EP | 1378545 A1 | 1/2004 |
| EP | 1612209 A1 | 1/2006 |
| JP | S-58-174448 A | 10/1983 |
| JP | H-08-184939 A | 7/1996 |
| JP | 2002-348494 A | 12/2002 |
| JP | 2008/505856 A | 2/2008 |
| JP | 52-41366 B | 7/2013 |
| WO | 2006/000573 | 1/2006 |
| WO | 2008/012322 A | 1/2008 |

OTHER PUBLICATIONS

International Preliminary Report on Patentability for PCT/EP2010/007287 dated Mar. 16, 2012.

* cited by examiner

CONCENTRATED STORAGE-STABLE AQUEOUS OPTICAL BRIGHTENING SOLUTIONS

The instant invention relates to concentrated aqueous solutions of specific triazinyl-stilbene based optical brighteners with excellent storage stability without the use of solubilizing auxiliaries, isolation or membrane filtration processes. The above mentioned brightening solutions provide superior fluorescent whitening effects when applied to the surface of paper in either the size-press or in a pigmented coating composition and show a reduced anionic charge.

PRIOR ART

The paper industry prefers to use optical brightening agents (OBAs) in the form of concentrated, aqueous solutions which can be conveniently and accurately metered. It is well known, however, that OBAs typically have a low solubility in water at ambient temperatures owing to the presence of inorganic salts which are formed as by-products of the manufacturing process.

To prevent such a drawback, Japanese Kokai 62-106965 discloses highly soluble triazinyl-stilbene based OBAs of the following compounds of formula (I)

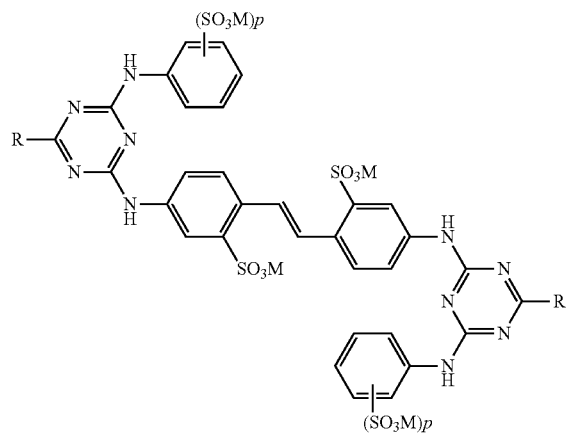

(I)

in which

M is typically an alkali metal atom, p is 0, 1 or 2 and

R is an amino acid residue from which a hydrogen atom of the amino group has been removed.

However, the high anionic charge generated by the amino acid residues can create a difficulty for papermakers who wish to recycle broke—that is, to repulp any paper waste generated in the paper making process—in that the optical brightener can be extracted in the repulping process leading to a build-up of anionic charge in the system which can interfere with cationic chemicals used, e.g. for sizing, or for retention and drainage purposes.

U.S. Pat. No. 4,466,900 describes a process for the preparation of storage stable aqueous solutions containing compounds of formula (I) which have a reduced anionic charge and in which M is typically an alkali metal atom, p is 2, and R is among others a diethylamino radical according to example 1, characterized by passing the reaction mixture through a semipermeable membrane in order to remove inorganic salts. Owing to this additional time- and cost-consuming step, the described process is economically disadvantageous.

CH-532,686 describes the preparation and isolation of compounds of formula (I) which have reduced anionic charge and in which M is typically an alkali metal atom, p is 2 and R is selected from di-alkylamino radicals. Di-n-propylamine is mentioned in table I, characterized by precipitation from the reaction mixture. The solid compounds of formula (I) thus obtained are directly used to brighten papers either at the size press or in a coating composition. However, in this patent there is no disclosure relating to the preparation of concentrated storage-stable aqueous solutions.

WO 2006/000573 A1 discloses storage stable concentrated solutions of optical brighteners derived from an aliphatic alkyl amine having a branched alkyl chain. Formula (10) discloses a hexasulphonated OBA derived from the secondary amine methyl-isopropyl-amine.

There is therefore a need for optical brighteners having a reduced anionic charge and from which concentrated storage-stable aqueous brightening solutions can be prepared without additional time- and cost-consuming steps such as membrane filtration, isolation or the addition of auxiliaries.

BRIEF DESCRIPTION OF THE DRAWING

FIG. 1 depicts an aqueous solution containing 0.150 mol per kg of compound of formula (6a) obtained according to example 6 from CH532686 (left) and compound of formula (6) obtained according to preparative example 2a from the present application (right). FIG. 1 clearly shows the advantage of storage stability of the aqueous solution provided by the instant invention.

DESCRIPTION OF THE INVENTION

Surprisingly, compounds of formula (1) combine a reduced anionic charge with a high storage-stability when prepared as concentrated aqueous solutions without the need for additional process steps or of solubilizing agents while providing superior fluorescent whitening effects when applied to the surface of paper in either the size-press or in a pigmented coating composition.

The present invention provides concentrated storage-stable aqueous solution (S) comprising components (a), (b) and (c), wherein
component (a) is at least one optical brightening agent of formula (1),

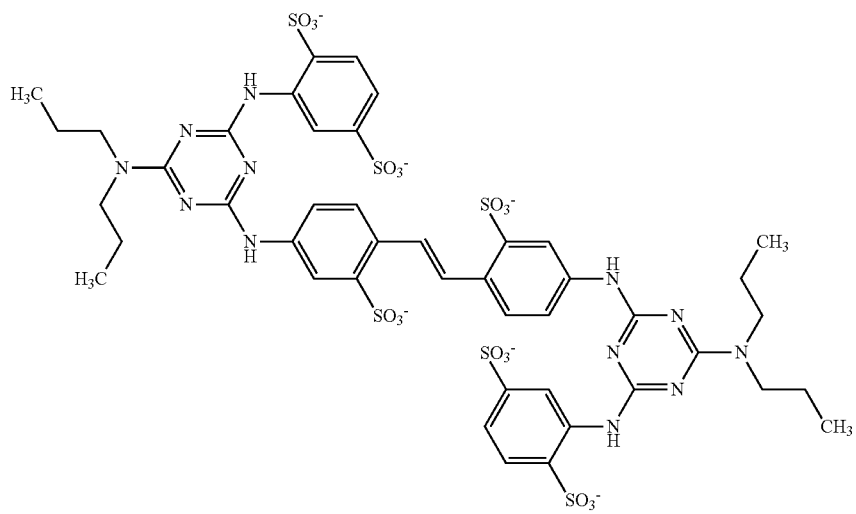

(1)

in which
the anionic charge on the brightener is balanced by a cationic charge composed of one or more cations selected from the group consisting of hydrogen, alkali metal cation, alkaline earth metal cation, ammonium, ammonium which is mono-, di- or trisubstituted by a $C_{1-4}$ linear or branched alkyl radical and ammonium which is mono-, di- or trisubstituted by a $C_{1-4}$ linear or branched hydroxyalkyl radical, with a concentration of component (a) of 0.08 to 0.3 mol per kg based on the weight of the concentrated storage-stable aqueous solution (S),
component (b) is at least one inorganic salt (SA), with a concentration of 2 to 15% by weight, based on the total weight of the concentrated storage-stable aqueous solution (S),
and
component (c) is water, with a concentration of 10% to 88% by weight, the % by weight based on the total weight of the concentrated storage-stable aqueous solution (S).

Optionally, the concentrated storage-stable aqueous solution (S) can contain polyethyleneglycol in an amount of from 2 to 40% by weight, % by weight based on the total weight of the concentrated storage-stable aqueous solution (S) to function as a so-called carrier in order to boost the performances of component (a).

Optionally, the concentrated storage-stable aqueous solution (S) can contain polyvinylalcohol in an amount of from 0.01 to 10% by weight, % by weight based on the total weight of the concentrated storage-stable aqueous solution (S) to function as a so-called carrier in order to boost the performances of component (a).

Preferred compounds of formula (1) are those in which the anionic charge on the brightener is balanced by a cationic charge composed of one or more cations selected from the group consisting of $Li^+$, $Na^+$, $K^+$, $Ca^{2+}$, $Mg^{2+}$ and ammonium which is mono-, di- or trisubstituted by a $C_{1-4}$ linear or branched hydroxyalkyl radical.

More preferred compounds of formula (1) are those in which the anionic charge on the brightener is balanced by a cationic charge composed of one or more cations selected from the group consisting of $Na^+$, $K^+$, $Ca^{2+}$, $Mg^{2+}$ and ammonium which is mono-, di- or trisubstituted by a $C_{1-4}$ linear or branched hydroxyalkyl radical.

Especially preferred compounds of formula (1) are those in which the anionic charge on the brightener is balanced by a cationic charge composed of one or more cations selected from the group consisting of $Na^+$ and $K^+$.

Preferably, if the anionic charge on the brightener is balanced by a cationic charge composed of more than one cation, this mixture of different cations comprises 2, 3, 4, or 5, more preferably 2, 3 or 4, even more preferably 2 or 3 different cations.

In a preferred aspect to the invention, the concentrated storage-stable aqueous solution (S) contains from 0.08 to 0.2 mol of component (a) per kg of concentrated storage-stable aqueous solutions (S), more preferably from 0.09 to 0.18 mol of component (a) per kg of concentrated storage-stable aqueous solution (S).

In a further preferred aspect of the invention, the concentrated storage-stable aqueous solution (S) contains 2.5 to 14% by weight, more preferably 2.5 to 12% by weight of inorganic salts (SA), the % by weight based on the total weight of the concentrated aqueous solution (S). Preferably, the salts (SA) are the by-products of the manufacturing process.

Preferred inorganic salts (SA) are alkali metal salts and alkaline earth metal salts, preferably lithium, sodium, potassium, calcium or magnesium salts, or a mixture of said compounds.

More preferably, inorganic salts (SA) are lithium halide, sodium halide or potassium halide or mixture of said compounds.

Even more preferably, inorganic salts (SA) are sodium chloride, potassium chloride or mixture of said compounds.

Further subject of the invention is a process for the preparation of concentrated storage-stable aqueous solution (S) as defined above, also in all their preferred embodiments, by stepwise reaction of a cyanuric halide with a) an amine of formula (2)

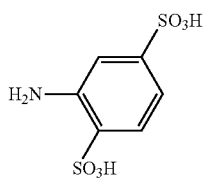

(2)

in the free acid, partial- or full salt form,
(b) a diamine of formula (3)

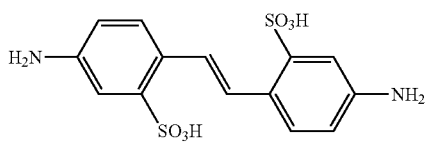

(3)

in the free acid, partial- or full salt form,
and
c) di-n-propylamine of formula (4),

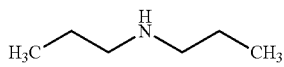

(4)

in the presence of water and using a base (B).

Preferably, the solution obtained from the manufacturing process is used directly for the preparation of the storage-stable aqueous solution (S), if necessary by dilution to the desired final concentration. Preferably, no further process steps such as membrane filtration, drying etc. are applied for the preparation of the concentrated storage-stable aqueous solution (S).

As a cyanuric halide there may be employed the fluoride, chloride or bromide. Cyanuric chloride is preferred.

Each reaction may be carried out in an aqueous medium, the cyanuric halide being suspended in water, or in an aqueous/organic medium, the cyanuric halide being dissolved in a solvent such as acetone. Each amine may be introduced without dilution, or in the form of an aqueous solution or suspension. The amines can be reacted with the cyanuric halide in any order, although it is preferred to react the aromatic amines first. A stoichiometric amount of the amine means half of the molar amount of cyanuric halide in case of the diamine of formula (3), and means an equivalent molar amount of the cyanuric halide in case of the amine of formula (2) and of the di-n-propylamine of formula (4). Each amine may be reacted stoichiometrically, or in excess, with regard to the cyanuric halide. Typically, the aromatic amines are reacted stoichimetrically, or in slight excess; the di-n-propylamine of formula (4) is generally employed in an excess of 0.1-30% over stoichiometry.

For substitution of the first halogen of the cyanuric halide, it is preferred to operate at a temperature in the range of 0 to 20° C. and under acidic to neutral pH conditions, more preferably in the pH range of 2 to 7. For substitution of the second halogen of the cyanuric halide, it is preferred to operate at a temperature in the range of 20 to 60° C. and under weakly acidic to weakly alkaline conditions, more preferably at a pH in the range of 4 to 8. For substitution of the third halogen of the cyanuric halide, it is preferred to operate at a temperature in the range of 60 to 102° C. and under weakly acidic to alkaline conditions, more preferably at a pH in the range of 7 to 10.

The reaction time for substitution of the first, the second and the third halogen of the cyanuric halide, e.g. by an aromatic amine of formula (2) and formula (3) and by a di-n-propylamine of formula (4) is in the range of from 10 minutes to 24 hours, preferably of from 30 minutes to 10 hours, more preferable of from 1 to 5 hours.

The pH of each reaction is generally controlled by addition of a suitable base (B), the choice of base (B) being dictated by the desired final composition of the concentrated storage-stable aqueous solution (S). Preferred bases (B) are, for example, alkali metal or alkaline earth metal (e.g. lithium, sodium, potassium, calcium, magnesium) hydroxides, carbonates or bicarbonates, or aliphatic tertiary amines, e.g. triethanolamine or triisopropanolamine, or combinations thereof. Where base (B) is a combination of two or more different bases, the bases may be added in any order, or at the same time.

Preferably, the salts (SA) are formed during the manufacturing process, e.g. by neutralization of hydrogen halide with a suitable base (B), for example according to equation 1 in which base (B) is sodium hydroxide.

$$NaOH + HCl \rightarrow NaCl + H_2O \qquad \text{(equation 1)}$$

Preferably, hydrogen halide is released during the three substitutions of cyanuric halide by, e.g. an aromatic amine of formula (2) and formula (3) and by di-n-propylamine of formula (4).

Where it is necessary to adjust the reaction pH, acids may be employed, examples of which include hydrochloric acid, sulphuric acid, formic acid and acetic acid.

Further subject of the invention therefore is the use of concentrated storage-stable aqueous solutions (S) as defined above, also in all their preferred embodiments, as optical brightening agents, preferably for optical brightening of cellulosic substrates, e.g. textiles, non-wovens or more preferably paper.

It is possible to use other optical brighteners, which are structurally different from formula (1), in addition to component (a).

For the optical brightening of textiles and non-wovens, the concentrated storage-stable aqueous solutions (S) may, for example, be employed in padding processes, where the brightener concentration in the treatment bath may be kept almost constant. In the finishing of textiles (fabrics or, preferably, non-woven fabrics) with binding agents, especially synthetic resins, the concentrated storage-stable aqueous solutions (S) may be added to the synthetic resin either in the treatment bath or before. The optical brightener may be fixed, and the finishing agent cross-linked, in accordance with the cold dwell process or by heat treatment, optionally after intermediate drying. Owing to their stability towards acids and salts, e.g. magnesium chloride and zinc chloride, the compounds of formula (1) in the form of their concentrated storage-stable aqueous solutions (S) are also suitable for the optical brightening and simultaneous crease-proof finishing of cotton. The concentrated storage-stable aqueous solutions (S) may be employed in an amount in the range of 0.01 to 2.5% by weight, preferably 0.02 to 2.0% by weight, the % by weight based on the weight of the dry cellulosic subtrate.

The concentrated storage-stable aqueous solutions (S) are more preferably suitable as optical brightening agents for the brightening of paper and non-wovens, even more preferably for optical brightening of paper after sheet formation, or of non-wovens after web formation.

Especially preferably, the concentrated storage-stable aqueous solutions (S) are suitable for the brightening of paper after sheet formation. This may be effected by adding the concentrated storage-stable aqueous solution (S) to a pigmented coating composition, or to a sizing solution or suspension. The paper may be of fine or coarse nature, and of bleached or unbleached cellulose.

For the treatment of paper in the size-press, sizing solutions or suspensions containing the concentrated storage-stable aqueous solution (S) in the range of 0.5 to 125 grams per liter of sizing solution or suspension, preferably 2 to 100 grams per liter may be used. The sizing solution or suspension may also contain one or more binding agents in a concentration of between 1 and 30% by weight, preferably between 2 and 20% by weight, most preferably between 5 and 15% by weight, the % by weight based on the weight of the sizing solution. The pH of the sizing solution or suspension is typically in the range 5-9, preferably 6-8.

The binding agent is selected from the group consisting of native starch, enzymatically modified starch, chemically modified starch and mixtures thereof. Modified starches are preferably oxidized starch, hydroxyethylated starch or acetylated starch. The native starch is preferably an anionic starch, a cationic starch, or an amphoteric starch. While the starch source may be any, preferably the starch sources are corn, wheat, potato, rice, tapioca or sago.

The sizing solution or suspension may optionally contain a divalent metal salt or a mixture of divalent metal salts differing from the inorganic salts (SA) contained in the concentrated storage-stable aqueous solution (S) in a concentration of between 1 and 100 g/l, preferably between 2 and 80 g/l, most preferably between 5 and 70 g/l sizing solution.

Preferred divalent metal salts are selected from the group consisting of calcium chloride, magnesium chloride, calcium bromide, magnesium bromide, calcium iodide, magnesium iodide, calcium nitrate, magnesium nitrate, calcium formate, magnesium formate, calcium acetate, magnesium acetate, calcium citrate, magnesium citrate, calcium gluconate, magnesium gluconate, calcium ascorbate, magnesium ascorbate, calcium sulphite, magnesium sulphite, calcium bisulphite, magnesium bisulphite, calcium dithionite, magnesium dithionite, calcium sulphate, magnesium sulphate, calcium thiosulphate, magnesium thiosulphate and mixtures of said compounds.

More preferred divalent metal salts are selected from the group consisting of calcium chloride, magnesium chloride, calcium bromide, magnesium bromide, calcium sulphate, magnesium sulphate, calcium thiosulphate, magnesium thiosulphate and mixtures of said compounds.

Especially preferred divalent metal salts are selected from the group consisting of calcium chloride, magnesium chloride, magnesium sulphate and mixtures of said compounds.

When the divalent metal salt is a mixture of one or more calcium salts and one or more magnesium salts, the amount of calcium salts may be in the range of 0.1 to 99.9% by weight based on the total weight of added divalent metal salts.

In addition to the concentrated storage-stable aqueous solution (S), the sizing solution or suspension may also contain one or more binders, water and optionally optical brighteners, which are structurally different from formula (1), and optionally one or more divalent metal salts. The sizing solution or suspension may contain by-products formed during the preparation of the component (a) as well as other additives conventionally used for the treatment of cellulosic substrates such as textiles, non-wovens or paper.

Examples of paper additives are secondary binders, anti-freezes, biocides, defoamers, wax emulsions, dyes, inorganic salts, preservatives, complexing agents, thickeners, surface sizing agents, cross-linkers, pigments, special resins etc.

The sizing composition is preferably prepared by adding the concentrated storage-stable aqueous solution (S) and, optionally, the divalent metal salt and/or any other components, to an aqueous solution of the binder, preferably at a temperature of between 20° C. and 90° C.

The sizing composition may be applied to the surface of a paper substrate by any surface treatment method known in the art. Examples of application methods of the sizing composition include size-press applications, calendar size application, tub sizing, coating applications and spraying applications. The preferred method of application of the sizing composition is at the size-press such as puddle size press. A preformed sheet of paper is passed through a two-roll nip which is flooded with the sizing composition. The paper absorbs some of the composition, the remainder being removed in the nip.

The paper substrate contains a web of cellulose fibres which may be sourced from any fibrous plant. Preferably the cellulose fibres are sourced from hardwood and/or softwood. The fibres may be either virgin fibres or recycled fibers, or any combination of virgin and recycled fibres.

Pigmented coating compositions are essentially aqueous compositions that contain at least one binder and one white pigment, in particular an opacifying white pigment, and may additionally contain further additives such as dispersing agents and defoamers.

Although it is possible to produce coating compositions that are free from white pigments, the best white substrates for printing are made using opaque coating compositions that contain 10 to 80% by weight, the % by weight based on the total weight of the opaque coating composition, of white pigment. Such white pigments are generally inorganic pigments, e.g., aluminium silicates (e.g. kaolin, otherwise known as china clay), calcium carbonate (e.g. chalk), titanium dioxide, aluminium hydroxide, barium carbonate, barium sulphate, or calcium sulphate (e.g. gypsum), or mixtures thereof.

The binders in the pigmented coating compositions may be any of those commonly used in the paper industry for the production of coating compositions and may consist of a single binder or of a mixture of primary and secondary binders. The sole or primary binder is preferably a synthetic latex, typically a styrene-butadiene, vinyl acetate, styrene acrylic, vinyl acrylic or ethylene vinyl acetate polymer. The secondary binder may be, e.g., starch, carboxymethylcellulose, casein, soy polymers, or polyvinyl alcohol.

The sole or primary binder is used in an amount typically in the range 5 to 25% by weight, the % by weight based on the total weight of white pigment. The secondary binder is used in an amount typically in the range 0.1 to 10% by weight, the % by weight based on the total weight of white pigment; starch however is typically used in the range 3 to 10% by weight, the % by weight based on the total weight of white pigment.

The concentrated storage-stable aqueous solutions (S) may be employed in an amount resulting in an amount of component (a) in the range of 0.01 to 3% by weight, preferably 0.05 to 2% by weight, the % by weight based on the weight of the white pigment.

The concentrated storage-stable aqueous solutions (S) containing optical brightening agents of formula (1) have the advantage of lower anionic charge compared to analogous compounds of the above mentioned Japanese Kokai 62-106965.

Surprisingly, the optical brightening agents of formula (1) also have higher solubility in water than analogous compounds in which the di-n-propylamino radicals of compounds of formula (1) are exchanged for di-n-ethylamino or di-n-butylamino radicals as exemplified in Patents CH 532, 686 and U.S. Pat. No. 4,466,900.

Surprisingly, the concentrated storage-stable aqueous solutions (S) show better applicational properties compared to the analogous compounds of the above mentioned Japanese Kokai 62-106965.

The following examples shall explain the instant invention in more detail. If not indicated otherwise, "%" and "parts" are meant to be % by weight and parts by weight.

EXAMPLES

Preparative Example 1

520.2 parts of aniline-2,5-disulphonic acid monosodium salt are added to 900 parts of water and dissolved with the aid of approx. 295.1 parts of an aqueous sodium hydroxide solution 30% w/w at approx. 25° C. and a pH of approx. 8 to 9. The so-formed solution is added over a period of approx. 30 minutes to 331.9 parts of cyanuric chloride dispersed in 405 parts of water and 630 parts of ice. The temperature is kept below 5° C. using an ice/water bath and the pH is maintained at approx. 4 to 5 using approx. 504.1 parts of an aqueous sodium carbonate solution 20% w/w. At the end of the addition, the pH is increased to approx. 6 using approx. 35.1 parts of an aqueous sodium carbonate solution 20% w/w and stirring is continued at approx. 0 to 5° C. until completion of the reaction. 151.2 parts of sodium bicarbonate are then added to the reaction mixture. An aqueous solution, obtained by dissolving under nitrogen 333.4 parts of 4,4'-diaminostilbene-2,2'-disulphonic acid in 1240 parts of water with the aid of approx. 235.8 parts of an aqueous sodium hydroxide solution 30% w/w at approx. 45 to 50° C. and a pH value of approx. 8 to 9, is dropped into the reaction mixture. The resulting mixture is stirred at approx. 45 to 50° C. until completion of the reaction. The resulting aqueous mixture contains compound of formula (5) at a concentration of 0.161 mol per kg of mixture.

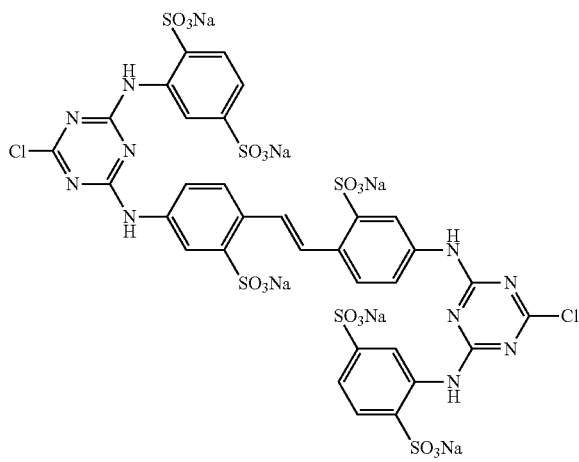

(5)

Preparative Example 2a

To 1234.5 parts of an aqueous mixture containing compound of formula (5) obtained according to preparative example 1 are added 42.5 parts of di-n-propylamine. The mixture is stirred at reflux for 2 hours, the pH being kept at 8 to 9 by the addition of an aqueous sodium hydroxide solution 30% w/w. The aqueous solution so-formed is cooled to 60 to 65° C. and filtered. Water is added to the filtrate or removed by distillation to give concentrated storage-stable aqueous solution 2a containing compound of formula (6) at a concentration of 0.150 mol per kg of the final concentrated storage-stable aqueous optical brightening solution 2a (20.4% by weight based on the total weight of the final concentrated storage stable aqueous optical brightening solution 2a) and approx. 5.3% by weight (% by weight based on the total weight of the final concentrated storage stable aqueous optical brightening solution 2a) of sodium chloride. The so-formed concentrated storage stable aqueous optical brightening solution 2a has a pH in the range 8 to 9 and shows no precipitation after 2 weeks at 5° C.

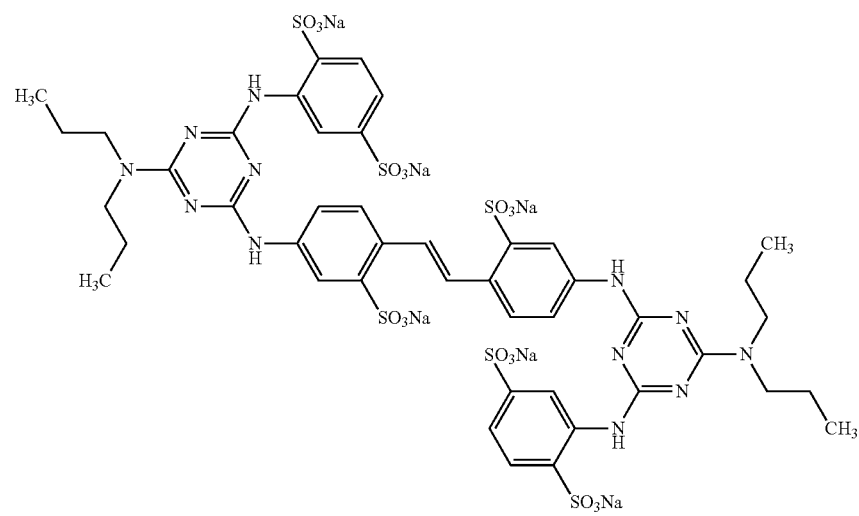

(6)

Preparative Example 2b

Concentrated storage-stable aqueous optical brightening solution 2b is produced by stirring together
- a concentrated aqueous optical brightening solution containing compound of formula (6) prepared according to preparative example 2a and
- a polyethylene glycol having an average molecular weight of 1500, while heating to 90 to 95° C. The parts of each component are selected in order to get a final concentrated storage-stable aqueous optical brightening solution 2b comprising a compound of formula (6) at a concentration of 0.150 mol per kg of the final concentrated storage-stable aqueous optical brightening solution 2b and 6% by weight of polyethylene glycol 1500 (% by weight based on the total weight of the final concentrated storage-stable aqueous optical brightening solution 2b). In order to get the desired concentration of each component in the final concentrated storage-stable aqueous optical brightening solution 2b, water is either added or removed by distillation. The concentrated storage-stable aqueous optical brightening solution 2b has a pH in the range 8 to 9 and contains approx. 5.3% by weight (% by weight based on the total weight of the final concentrated storage-stable aqueous optical brightening solution 2b) of sodium chloride. The concentrated storage-stable aqueous optical brightening solution 2b obtained following this procedure shows no signs of precipitation after 2 weeks at 5° C.

Comparative Example 2c

Compound of formula (6a) is obtained as a powder by following the same procedure as in example 6 from CH532686, the anionic charges on the optical brightener being balanced by $Na^+$ and/or $K^+$ cations.

Along with compound of formula (6a), the powder contains 1.9% by weight of sodium cation, 7.5% by weight of potassium cation, 5.1% by weight of chloride anion and 1.3% by weight of water (% by weight based on the total weight of the final obtained powder).

An aqueous mixture containing compound of formula (6a) at a concentration of 0.150 mol per kg is prepared by adding the powder containing compound of formula (6a) obtained as in example 6 from CH532686 in water and stirring for 1 hour.

(Picture 1 see appendix).

Comparative Example 3

An aqueous optical brightening solution 3 containing compound of formula (7) at a concentration of 0.150 mol per kg of the final aqueous optical brightening solution 3 (19.6% by weight based on the total weight of the final aqueous optical brightening solution 3) and approx. 5.3% by weight (% by weight based on the total weight of the final aqueous optical brightening solution 3) of sodium chloride is obtained following the same procedure as in preparative example 2a with the sole difference that 30.7 parts of diethylamine are used instead of 42.5 parts of di-n-propylamine. The so-formed aqueous optical brightening solution 3 has a pH in the range 8 to 9 and shows precipitation within 0 to 4 days at 5° C.

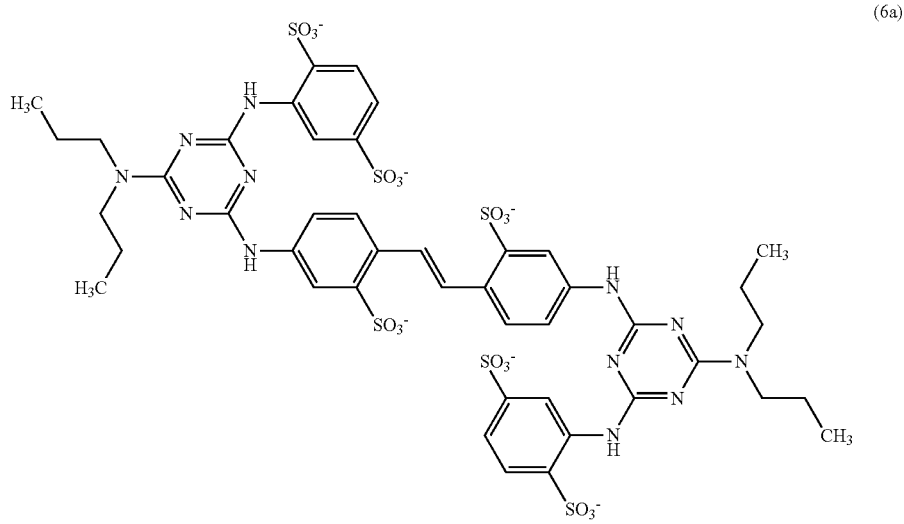

(6a)

(7)

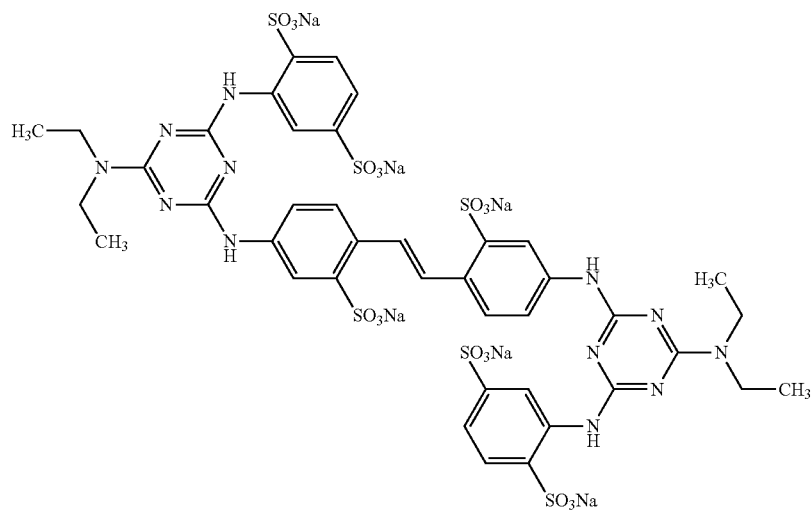

Comparative Example 4

An aqueous optical brightening solution 4 containing compound of formula (8) at a concentration of 0.150 mol per kg of the final aqueous optical brightening solution 4 (21.3% by weight based on the total weight of the final aqueous optical brightening solution 4) and approx. 5.3% by weight (% by weight based on the total weight of the final aqueous optical brightening solution 4) of sodium chloride was obtained following the same procedure as in preparative example 2a with the sole difference that 54.3 parts of di-n-butylamine are used instead of 42.5 parts of di-n-propylamine. The so-formed aqueous optical brightening solution 4 has a pH in the range 8 to 9 and shows precipitation within 0 to 4 days at 5° C.

Comparative Example 5a

An aqueous optical brightening solution 5a containing compound of formula (9) at a concentration of 0.150 mol per kg of the final aqueous optical brightening solution 5a (22.7% by weight based on the total weight of the final aqueous optical brightening solution 5a) and approx. 5.3% by weight (% by weight based on the total weight of the final aqueous optical brightening solution 5a) of sodium chloride is obtained following the same procedure as in preparative example 2a with the sole difference that 55.9 parts of L-aspartic acid are used instead of 42.5 parts of di-n-propylamine. The so-formed aqueous optical brightening solution 5a has a pH in the range 8 to 9 and shows no signs of precipitation after 2 weeks at 5° C.

(8)

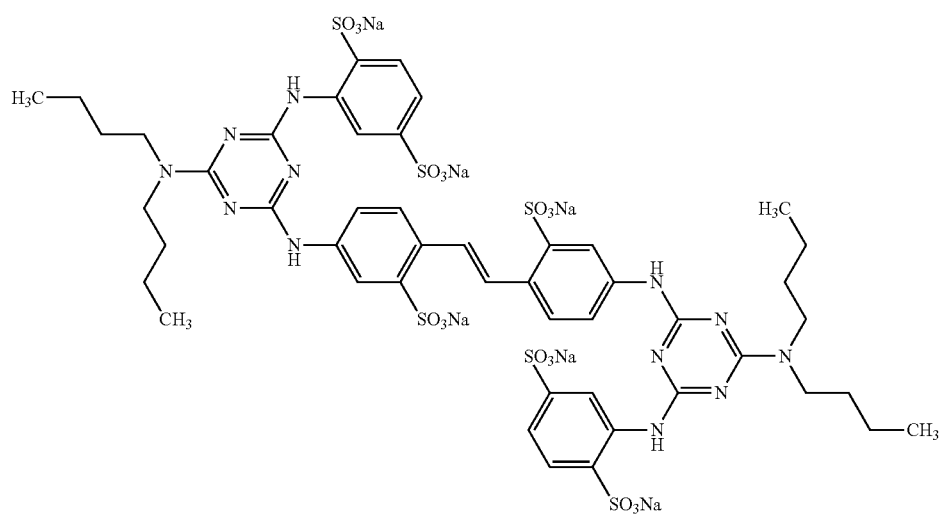

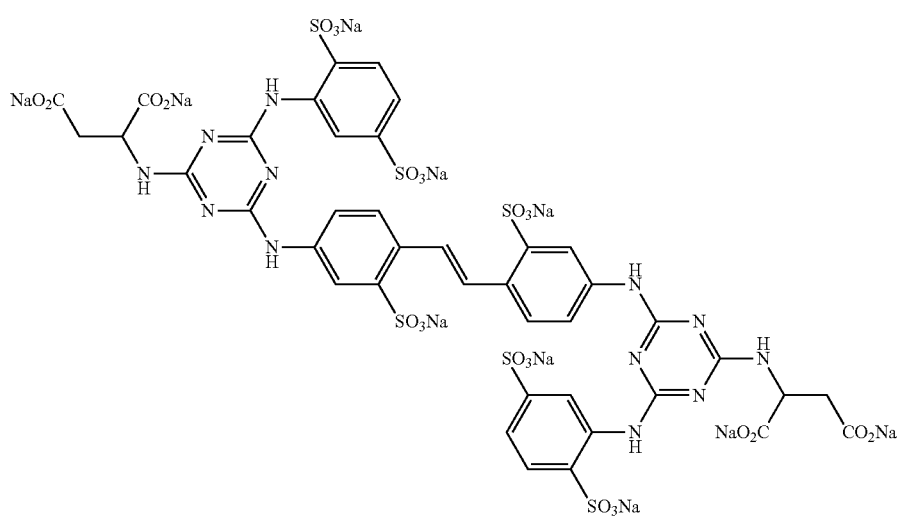

(9)

Comparative Example 5b

An aqueous optical brightening solution 5b is produced by stirring together
- an aqueous solution containing compound of formula (9) prepared according to comparative example 5a and
- a polyethylene glycol having an average molecular weight of 1500, while heating to 90 to 95° C. The parts of each component are selected in order to get a final aqueous optical brightening solution 5b comprising a compound of formula (9) at a concentration of 0.150 mol per kg of the final aqueous optical brightening solution 5b and 6% by weight of polyethylene glycol 1500 (% by weight based on the total weight of the final aqueous optical brightening solution 5b). In order to get the desired concentration of each component in the final aqueous optical brightening solution 5b, water is either added or removed by distillation. The aqueous optical brightening solution 5b has a pH in the range 8 to 9 and contains approx. 5.3% by weight (% by weight based on the total weight of the final aqueous brightening solution 5b) of sodium chloride. The aqueous optical brightening solution 5b obtained following this procedure shows no signs of precipitation after 2 weeks at 5° C.

Comparative Example 6a

An aqueous optical brightening solution 6a containing compound of formula (10) disclosed in WO 2006/000573 A1 at a concentration of 0.150 mol per kg of the final aqueous optical brightening solution 6a (19.6% by weight based on the total weight of the final aqueous optical brightening solution 6a) and approx. 5.3% by weight (% by weight based on the total weight of the final aqueous optical brightening solution 6a) of sodium chloride is obtained following the same procedure as in preparative example 2a with the sole difference that 30.7 parts of N-methyl-N-isopropylamine are used instead of 42.5 parts of di-n-propylamine. The so-formed aqueous optical brightening solution 6a has a pH in the range 8 to 9 and shows precipitation within 1 to 5 days at 5° C.

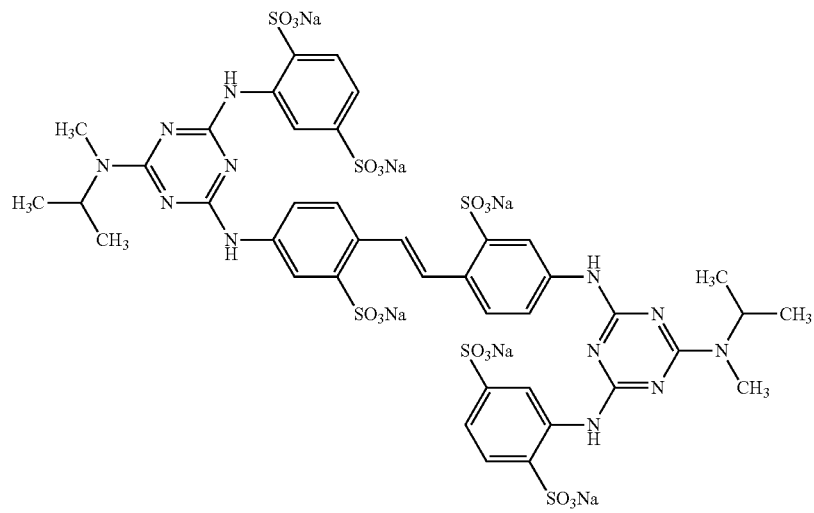

(10)

Comparative Example 6b

An aqueous optical brightening solution 6b is produced by stirring together
- an aqueous solution containing compound of formula (10) prepared according to comparative example 6a and
- a polyethylene glycol having an average molecular weight of 1500, while heating to 90 to 95° C. The parts of each component are selected in order to get a final aqueous optical brightening solution 6b comprising a compound of formula (10) at a concentration of 0.150 mol per kg of the final aqueous optical brightening solution 6b and 6% by weight of polyethylene glycol 1500 (% by weight based on the total weight of the final aqueous optical brightening solution 6b). In order to get the desired concentration of each component in the final aqueous optical brightening solution 6b, water is either added or removed by distillation. The aqueous optical brightening solution 6b has a pH in the range 8 to 9 and contains approx. 5.3% by weight (% by weight based on the total weight of the final aqueous optical brightening solution 6b) of sodium chloride. The aqueous optical brightening solution 6b obtained following this procedure shows precipitation within 1 week at 5° C.

Application Example 2a and Comparative Application Example 5a

Sizing solutions are prepared by adding one of the aqueous optical brightening solutions containing
- compound of formula (6) prepared according to preparative example 2a and
- compound of formula (9) prepared according to comparative example 5a, respectively at a range of concentrations of from 0 to 80 g/l (of from 0 to approx. 20 g/l based on dry optical brightener) to a stirred, aqueous solution containing calcium chloride (30 g/l) and an anionic potato starch (50 g/l) (Perfectamyl A4692 from AVEBE B.A.) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier. The dried paper is allowed to condition, and then measured for CIE whiteness and for a* and b* values on a calibrated Auto Elrepho spectrophotometer. The results are shown in table 1 and table 2 respectively and clearly show the superior whiteness build-up and improved shade development provided by the instant invention.

TABLE 1

| CIE Whiteness | | |
|---|---|---|
| OBA solution | Examples | |
| [g/l] | 2a | 5a |
| 0 | 104.3 | 104.3 |
| 20 | 135.2 | 134.3 |
| 40 | 139.9 | 138.6 |
| 60 | 141.2 | 137.8 |
| 80 | 143.1 | 135.2 |

TABLE 2

| CIELAB a* and b* values | | | | |
|---|---|---|---|---|
| | Examples | | | |
| OBA solution | 2a | | 5a | |
| [g/l] | a* | b* | a* | b* |
| 0 | 1.19 | −3.59 | 1.19 | −3.59 |
| 20 | 2.36 | −9.95 | 2.30 | −9.89 |
| 40 | 2.65 | −10.18 | 2.01 | −10.73 |
| 60 | 2.55 | −11.40 | 1.53 | −10.49 |
| 80 | 2.61 | −11.82 | 0.92 | −9.77 |

Application Example 2b and Comparative Application Example 5b

Sizing solutions are prepared by adding one of the aqueous optical brightening solutions containing
- compound of formula (6) prepared according to preparative example 2b and
- compound of formula (9) prepared according to comparative example 5b, respectively at a range of concentrations of from 0 to 80 g/l (of from 0 to approx. 20 g/l based on dry optical brightener) to a stirred, aqueous solution containing calcium chloride (30 g/l) and an anionic potato starch (50 g/l) (Perfectamyl A4692 from AVEBE B.A.) at 60° C. The sizing solution is allowed to cool, then poured between the moving rollers of a laboratory size-press and applied to a commercial 75 g/m$^2$ AKD (alkyl ketene dimer) sized, bleached paper base sheet. The treated paper is dried for 5 minutes at 70° C. in a flat bed drier. The dried paper is allowed to condition, and then measured for CIE whiteness and for a* and b* values on a calibrated Auto Elrepho spectrophotometer. The results are shown in table 3 and table 4 respectively and clearly show the superior whiteness build-up and improved shade development provided by the instant invention.

TABLE 3

| CIE Whiteness | | |
|---|---|---|
| OBA solution | Examples | |
| [g/l] | 2b | 5b |
| 0 | 104.3 | 104.3 |
| 20 | 137.3 | 136.1 |
| 40 | 141.5 | 139.9 |
| 60 | 143.5 | 138.2 |
| 80 | 144.5 | 136.8 |

TABLE 4

| CIELAB a* and b* values | | | | |
|---|---|---|---|---|
| | Examples | | | |
| OBA solution | 2b | | 5b | |
| [g/l] | a* | b* | a* | b* |
| 0 | 1.19 | −3.59 | 1.19 | −3.59 |
| 20 | 2.83 | −10.67 | 2.35 | −10.29 |
| 40 | 2.87 | −11.11 | 2.03 | −11.01 |
| 60 | 3.03 | −11.99 | 1.53 | −10.51 |
| 80 | 2.93 | −12.15 | 1.11 | −10.13 |

Application Example 3

A coating composition is prepared containing 70 parts chalk (commercially available under the trade name Hydrocarb 90 from OMYA), 30 parts clay (commercially available under the trade name Kaolin SPS from IMERYS), 42.8 parts water, 0.6 parts dispersing agent (a sodium salt of a polyacrylic acid commercially available under the trade name Polysalz S from BASF), 20 parts of 50% latex (a styrene butadiene copolymer commercially available under the trade name DL 921 from Dow), 8 parts of a 10 wt % aqueous solution of polyvinyl alcohol (0.8 part of dry polyvinyl alcohol) having a degree of hydrolysis of 98-99% and a Brookfield viscosity of 4.0-5.0 mPa·s (4% aqueous solution at 20° C.). The solids content of the coating composition is adjusted to approx. 65% by the addition of water, and the pH is adjusted to 8-9 with sodium hydroxide.

Aqueous optical brightening solutions 2a, 2b, 5a and 5b, made as described in Preparative Examples 2a and 2b and Comparative Examples 5a and 5b respectively, are added at a range of concentrations from 0.8 to 2.0% by weight of dry solids to the stirred coating composition. The brightened coating composition is then applied to a commercial 75 gsm neutral-sized white paper base sheet using an automatic wire-wound bar applicator with a standard speed setting and a standard load on the bar. The coated paper is then dried for 2 minutes in a hot air flow. The dried paper is allowed to condition, then measured for CIE Whiteness and for CIELAB a* and b* values on a calibrated Auto Elrepho spectrophotometer. The results are shown in table 5 and 6 respectively and clearly show the superior whiteness build-up and improved shade development provided by the instant invention.

TABLE 5

| Conc. of OBA solutions by weight of dry solid (%) | Examples | | Comparative examples | |
|---|---|---|---|---|
| | 2a | 2b | 5a | 5b |
| 0 | 88.7 | 88.7 | 88.7 | 88.7 |
| 0.8 | 116.1 | 116.3 | 116.0 | 116.3 |
| 1.2 | 119.3 | 120.7 | 118.4 | 120.4 |
| 1.6 | 121.5 | 123.0 | 118.2 | 121.5 |
| 2.0 | 122.1 | 124.2 | 116.6 | 121.5 |

CIE Whiteness

TABLE 6

CIELAB a* and b* values

| Conc. of OBA solutions by weight of dry solid (%) | Examples | | | | Comparative examples | | | |
|---|---|---|---|---|---|---|---|---|
| | 2a | | 2b | | 5a | | 5b | |
| | a* | b* | a* | b* | a* | b* | a* | b* |
| 0 | 0.23 | 0.20 | 0.23 | 0.20 | 0.23 | 0.20 | 0.23 | 0.20 |
| 0.8 | 1.83 | −5.61 | 1.85 | −5.75 | 1.57 | −5.61 | 1.68 | −5.73 |
| 1.2 | 1.98 | −6.37 | 2.07 | −6.69 | 1.41 | −6.05 | 1.68 | −6.52 |
| 1.6 | 2.00 | −6.83 | 2.16 | −7.17 | 0.91 | −5.90 | 1.47 | −6.70 |
| 2.0 | 1.90 | −6.92 | 2.15 | −7.40 | 0.42 | −5.47 | 1.13 | −6.64 |

Application Example 4

Sizing solutions are prepared by adding one of the aqueous optical brightening mixtures containing compound of formula (6a) prepared according to comparative example 2c and compound of formula (6) prepared according to preparative example 2a, respectively at a range of concentrations of from 0 to 60 g/l (of from 0 to approx. 20 g/l based on dry optical brightener) to a stirred, aqueous solution containing an anionic potato starch (50 g/l) (Perfectamyl A4692 from AVEBE B.A.) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in table 7 and clearly show the superior whiteness build-up provided by the instant invention.

TABLE 7

CIE Whiteness

| OBA solution [g/l] | Examples | |
|---|---|---|
| | 2a | 2c |
| 0 | 101.2 | 101.2 |
| 10 | 121.7 | 121.7 |
| 20 | 130.4 | 128.9 |
| 30 | 135.0 | 133.3 |
| 40 | 137.8 | 135.6 |
| 60 | 141.2 | 139.0 |

The invention claimed is:

1. A concentrated storage-stable aqueous solution (S) comprising components (a), (b) and (c),
   wherein
   component (a) is at least one optical brightening agent of formula (1),

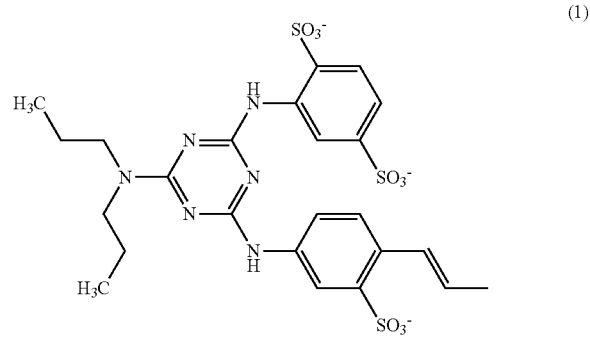

(1)

-continued

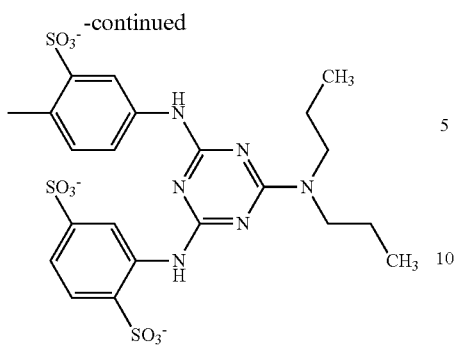

wherein
the anionic charge on the optical brightening agent is balanced by a cationic charge composed of one or more cations selected from the group consisting of hydrogen, alkali metal cation, alkaline earth metal cation, ammonium, ammonium which is mono-, di- or trisubstituted by a $C_{1-4}$ linear or branched alkyl radical and ammonium which is mono-, di- or trisubstituted by a $C_{1-4}$ linear or branched hydroxyalkyl radical,
and
the concentration of component (a) is 0.08 to 0.3 mol per kg, based on the total weight of the concentrated storage-stable aqueous solution (S),
component (b) is at least one inorganic salt (SA), in a concentration of 2 to 15% by weight, based on the total weight of the concentrated storage-stable aqueous solution (S),
and
component (c) is water, in a concentration of 10% to 88% by weight, based on the total weight of the concentrated storage-stable aqueous solution (S).,
wherein the concentrated storage-stable aqueous solution (S) shows no precipitation after two weeks at 5° C.

2. The concentrated storage-stable aqueous solution (S) according to claim 1, further comprising polyethyleneglycol in an amount of 2 to 40% by weight, %, based on the total weight of the concentrated storage-stable aqueous solution (S).

3. The concentrated storage-stable aqueous solution (S) according to claim 1, further comprising polyvinylalcohol in an amount of from 0.01 to 10% by weight, based on the total weight of the concentrated storage-stable aqueous solution (S).

4. The concentrated storage-stable aqueous solution (S) according to claim 1, wherein the anionic charge on the optical brightening agent of formula (1) is balanced by a cationic charge composed of one or more cations selected from the group consisting of Li +, Na +, K +, Ca 2+, Mg 2+ and ammonium which is mono-, di- or trisubstituted by a $C_{1-4}$ linear or branched hydroxyalkyl radical.

5. The concentrated storage-stable aqueous solution (S) according to claim 1, wherein the concentration of component (a) is 0.08 to 0.2 mol per kg of concentrated storage-stable aqueous solution (S).

6. The concentrated storage-stable aqueous solution (S) according to claim 1, wherein the concentration of the inorganic salt (SA)/component (b) is 2.5 to 14% by weight, based on the total weight of the concentrated aqueous solution (S) and that the salts (SA) are the by-products of the manufacturing process.

7. The concentrated storage-stable aqueous solution (S) according to claim 1, wherein the at least one inorganic salt (SA) is an alkali metal salt, alkaline earth metal salts or a combination thereof.

8. A process for the preparation of a concentrated storage-stable aqueous solution (S) according to claim 1, comprising the stepwise reaction of a cyanuric halide with
a) an amine of formula (2)

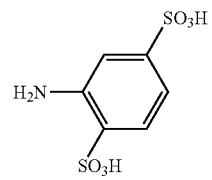

(2)

in the free acid, partial- or full salt form,
(b) a diamine of formula (3)

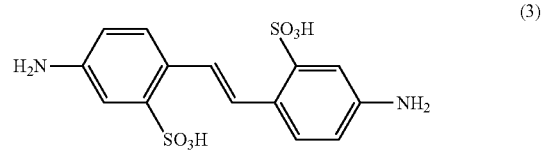 [SMILES: Nc1ccc(/C=C/c2ccc(N)cc2S(=O)(=O)O)c(S(=O)(=O)O)c1]

(3)

in the free acid, partial- or full salt form,
and
c) a di-n-propylamine of formula (4),

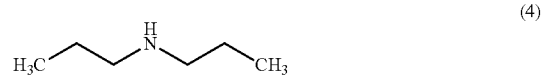

(4)

in the presence of water and using a base (B).

9. The process according to claim 8, wherein the cyanuric halide is fluoride, chloride or bromide.

10. The process according to claim 8, wherein the cyanuric halide is suspended in water, or in an aqueous/organic medium.

11. The process according to claim 8, wherein the aromatic amines (2) and (3) are reacted stoichiometrically or in slight excess and the di-n-propylamine (4) is employed in an excess of 0.1-30% over stoichiometry.

12. The process according to claim 8, wherein the first reaction step is carried out at a temperature in the range from 0 to 20° C., the second reaction step is carried out at a temperature in the range from 20 to 60° C. and the third reaction step is carried out at a temperature in the range from 60 to 102° C.

13. The process according to claim 1, wherein the first reaction step is carried out under acidic to neutral conditions, the second reaction step is carried out under weakly acidic to weakly alkaline conditions and the third reaction step is carried out under weakly acidic to alkaline conditions.

14. The process according to claim 8, wherein the base (B) is an alkali metal, alkaline earth metal hydroxide, carbonate, bicarbonate, an aliphatic tertiary amine or a combination thereof.

15. A brightened cellulosic substrate, textile or non-woven material brightened by the concentrated storage stable solution as claimed in claim 1.

16. The brightened cellulosic substrate, textile or non woven material according to claim 15, wherein the concentrated storage stable solution (S) is employed in an amount of 0.01 to 2.5% by weight based on the weight of the cellulosic substrate, textile or non-woven material.

17. A method for the treatment of paper in size-press, sizing solutions or suspensions comprising applying a concentrated storage stable solution as claimed in claim 1 in a concentration of 0.5 to 125 grams per liter of sizing solution or suspension.

18. A sizing solution or suspension for the treatment of paper, comprising a concentrated storage-stable solution (S) according to claim 1.

19. The sizing solution or suspension according to claim 18, wherein the concentrated storage stable solution solution (S) is contained in a concentration of 0.5 to 125 grams per liter of sizing solution or suspension.

20. The sizing solution according to claim 18, further comprising one or more binding agents, selected from the following group consisting of: native starch, enzymatically modified starch, chemically modified starch or-and mixtures thereof.

21. The sizing solution according to claim 18, further comprising a divalent metal salt or a mixture of divalent metal salts, which are different from the salt (SA).

22. The sizing solution according to claim 18, further comprising one or more binders, water and optionally other optical brighteners, which are structurally different from formula (1).

23. Pigmented coating composition comprising a concentrated storage-stable solution (S) according to claim 1.

24. The concentrated storage-stable aqueous solution (S) according to claim 1, wherein the concentration of component (a) is 0.09 to 0.18 mol per kg of concentrated storage-stable aqueous solution (S).

25. The concentrated storage-stable aqueous solution (S) according to claim 1, wherein the concentration of the inorganic salt (SA)/component (b) is 2.5 to 12% by weight based on the total weight of the concentrated aqueous solution (S) and that the salts (SA) are the by-products of the manufacturing process.

26. The concentrated storage-stable aqueous solution (S) according to claim 1, wherein the at least one inorganic salt (SA) is a lithium, sodium, potassium, calcium, or magnesium salt, or a mixture of said compounds.

* * * * *